US012649771B2

(12) United States Patent
Song et al.

(10) Patent No.: US 12,649,771 B2
(45) Date of Patent: Jun. 9, 2026

(54) MICROORGANISM EXPRESSING VASOACTIVE INTESTINAL PEPTIDE, AND USE THEREOF

(71) Applicant: MEDYTOX INC., Cheongju-si (KR)

(72) Inventors: Ji Yoon Song, Seongnam-si (KR); Hyo Jeong Choi, Anyang-si (KR); Hyeon Jin Noh, Seoul (KR); Young Ha Park, Suwon-si (KR); Yi Reh Jung, Uiwang-si (KR)

(73) Assignee: MEDYTOX INC., Cheongju-si (KR)

( * ) Notice: Subject to any disclaimer, the term of this patent is extended or adjusted under 35 U.S.C. 154(b) by 709 days.

(21) Appl. No.: 17/996,436

(22) PCT Filed: Apr. 9, 2021

(86) PCT No.: PCT/KR2021/004479
§ 371 (c)(1),
(2) Date: Oct. 18, 2022

(87) PCT Pub. No.: WO2021/215717
PCT Pub. Date: Oct. 28, 2021

(65) Prior Publication Data
US 2024/0218039 A1　　Jul. 4, 2024

(30) Foreign Application Priority Data

Apr. 20, 2020　　(KR) ........................ 10-2020-0047660

(51) Int. Cl.
| *A61P 1/00* | (2006.01) |
| *A61K 35/747* | (2015.01) |
| *A61P 29/00* | (2006.01) |
| *C07K 14/575* | (2006.01) |
| *C12N 15/74* | (2006.01) |

(52) U.S. Cl.
CPC ...... *C07K 14/57563* (2013.01); *A61K 35/747* (2013.01); *A61P 1/00* (2018.01); *A61P 29/00* (2018.01)

(58) Field of Classification Search
CPC .............. C07K 14/57563; C07K 14/72; A61K 35/747; A61P 1/00; A61P 29/00; C12N 15/746; C12N 15/74
See application file for complete search history.

(56) References Cited

U.S. PATENT DOCUMENTS

| 8,748,381 | B2 | 6/2014 | Polk et al. |
| 9,561,262 | B2 | 2/2017 | Georgopoulos et al. |
| 9,700,598 | B2 | 7/2017 | Sadeghi et al. |
| 10,064,902 | B2 | 9/2018 | Legrain-Raspaud et al. |
| 11,046,984 | B2 | 6/2021 | Mccoy et al. |
| 2011/0150907 | A1 | 6/2011 | Seegers et al. |
| 2016/0045557 | A1 | 2/2016 | Legrain-Raspaud et al. |
| 2018/0008677 | A1 | 1/2018 | Sadeghi et al. |
| 2019/0262420 | A1 | 8/2019 | Shailubhai |
| 2020/0339637 | A1 | 10/2020 | Kim et al. |

FOREIGN PATENT DOCUMENTS

| CN | 108753670 | A | 11/2018 |
| JP | 2000236873 | A | 9/2000 |
| JP | 2002154976 | A | 5/2002 |
| JP | 2006262724 | A | 10/2006 |
| JP | 2015529453 | A | 10/2015 |
| JP | 2016514670 | A | 5/2016 |
| JP | 2017515455 | A | 6/2017 |
| KR | 20120062777 | A | 6/2012 |
| KR | 1020140000620 | A | 1/2014 |
| KR | 20150095717 | A | 8/2015 |
| KR | 101992345 | B1 | 9/2019 |
| WO | 2008104890 | A2 | 9/2008 |
| WO | 2011086172 | A1 | 7/2011 |
| WO | 2014018596 | A2 | 1/2014 |
| WO | 2018097402 | A1 | 5/2018 |
| WO | 2019132231 | A1 | 7/2019 |

OTHER PUBLICATIONS

Xu et al., CN 108753670 A—PTO English Machine Translation attached; total pp. 1-11. (Year: 2018).*
A. Miyoshi et al., "Controlled Production of Stable Heterologous Proteins in Lactococcus Lactis", Applied and Environmental Microbiology, Jun. 2002, p. 3141-3146.
1st Office Action issued dated Sep. 19, 2023 of Japanese Patent Application No. 2022-563907.
Chun-Lan Xu et al., "Recombinant expressed vasoactive intestinal peptide analogue ameliorates TNBS-induced colitis in rats", World Journal of Gastroenterology, Feb. 14, 2018;24(b): 706-715.
European Search Report for European Patent Application No. 21793347.2 dated Mar. 22, 2024.
Manpreet Bains et al., "Vasoactive Intestinal Peptide Deficiency is associated with Altered Gut Microbiota Communities in Male and Female C57BL/6 Mice", Frontiers in Microbiology, Dec. 2019, vol. 10, Article 2689, 1-14.
Mari Iwasaki et al., "Recent advances in vasoactive intestinal peptide physiology and pathophysiology: focus on the gastrointestinal system [version 1; peer review: 4 approved]", F1000Resarch, Sep. 12, 2019, 1-13.
C. Michon et al., "Display of recombinant proteins at the surface of lactic acid bacteria: strategies and applications," Michon et al. Microb Cell Fact, 2016, pp. 1-16.
Catalina Abad et al., "Therapeutic Effects of Vasoactive Intestinal Peptide in theTrinitrobenzene Sulfonic Acid Mice Model of Crohn's Disease," Gastroenterology, 2003, pp. 961-971, vol. 124.
Haryoung Poo et al., "Oral administration of human papillomavirus type 16 E7 displayedon Lactobacillus casei induces E7-specific antitumor effects in C57/BL6 mice," Int. J. Cancer, 2006, pp. 1702-1709, vol. 119.

(Continued)

*Primary Examiner* — Satyendra K Singh
(74) *Attorney, Agent, or Firm* — CANTOR COLBURN LLP

(57) ABSTRACT

Provided are a recombinant microorganism expressing a vasoactive intestinal peptide (VIP) gene, and a composition including the microorganism for preventing or treating a disease causing damage to the gastrointestinal tract.

9 Claims, 9 Drawing Sheets

Specification includes a Sequence Listing.

(56)            References Cited

OTHER PUBLICATIONS

Mays et al., Curr. Opin. Biotechnol, 53: 224-231 (2018, published Mar. 15, 2018).

Mario Delgado et al., "In Vivo Delivery of Lentiviral Vectors Expressing Vasoactive Intestinal Peptide Complementary DNA as Gene Therapy for Collagen-Induced Arthritis," Arthritis & Rheumatism, Apr. 4, 2008, pp. 1026-1037, vol. 58, No. 4.

Rajasree et al., Ind. J. Geo-Marine Sc. 42(5): 766-775 (2015).

Sujin Bao, et al. "Distribution Dynamics of Recombinant Lactobacillus in the Gastrointestinal Tract of Neonatal Rats," Plos One, Mar. 27, 2013, pp. 1-8 (e60007), vol. 8, Issue 3.

Valéria Dellaretti Guimarães et al., "Use of Native Lactococci as Vehicles for Delivery of DNA into Mammalian Epithelial Cells," Applied and Environmental Microbiology, Nov. 2006, pp. 7091-7097, vol. 72, No. 11.

Wikipedia, https://en.wikipedia.org/wiki/M17_agar (accessed May 22, 2024).

Yan et al., Int. J Clin. Exp. Med. 8(11): 20245-20253 (2015).

Zachary Js Mays et al., "Synthetic biology in probiotic lactic acid bacteria: At the frontier of living therapeutics," Current Opinion in Biotechnology, Mar. 15, 2018, pp. 224-231, vol. 53.

Kalpana Sriraman et al., HtrA is Essential for Efficient Secretion of Recombinant Proteins by Lactococcus lactis, Applied and Environmental Microbiology, Dec. 2008, p. 7442-7446.

Mengjin Liu et al., "The proteolytic system of lactic acid bacteria revisited: a genomic comparison", Genomics 2010, 11:36.

Willem M. de Vos, "Gene expression systems for lactic acid bacteria", Ecology and industrial microbiology, current Opinion in Microrbiology, 1999, 2, pp. 289-295.

Chunlan Xu et al., "Biosynthesis of Polysaccharides-Capped Selenium Nanoparticles Using Lactococcus lactis NZ9000 and Their Antioxidant and Anti-inflammatory Activities", Frontiers in Microbiology, Jul. 1, 2019 vol. 10 Article 1632, pp. 1-12.

* cited by examiner

SEQUENCE LISTING

```
<160> NUMBER OF SEQ ID NOS: 34

<210> SEQ ID NO 1
<211> LENGTH: 28
<212> TYPE: PRT
<213> ORGANISM: Homo sapiens

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 28
<212> TYPE: PRT
<213> ORGANISM: Artificial Sequence
<220> FEATURE:
<223> OTHER INFORMATION: VIP variant 1
```

```
<400> SEQUENCE: 2

His Ser Asp Ala Val Phe Thr Asp Asn Tyr Thr Arg Leu Arg Arg Gln
1               5                   10                  15

Leu Ala Val Arg Arg Tyr Leu Asn Ser Ile Leu Asn
            20                  25

<210> SEQ ID NO 3
<211> LENGTH: 30
<212> TYPE: PRT
<213> ORGANISM: Artificial Sequence
<220> FEATURE:
<223> OTHER INFORMATION: VIP variant 2

<400> SEQUENCE: 3

His Ser Asp Ala Val Phe Thr Ala Asn Tyr Thr Arg Leu Arg Arg Gln
1               5                   10                  15

Leu Ala Val Arg Arg Tyr Leu Ala Ala Ile Gly Leu Arg Arg
            20                  25                  30

<210> SEQ ID NO 4
<211> LENGTH: 25
<212> TYPE: PRT
<213> ORGANISM: Artificial Sequence
<220> FEATURE:
<223> OTHER INFORMATION: VIP variant 3

<400> SEQUENCE: 4

Phe Thr Ala Asn Tyr Thr Arg Leu Arg Arg Gln Leu Ala Val Arg Arg
1               5                   10                  15

Tyr Leu Ala Ala Ile Leu Gly Arg Arg
            20                  25

<210> SEQ ID NO 5
<211> LENGTH: 28
<212> TYPE: PRT
<213> ORGANISM: Artificial Sequence
<220> FEATURE:
<223> OTHER INFORMATION: VIP variant 4

<400> SEQUENCE: 5

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Asn
            20                  25

<210> SEQ ID NO 6
<211> LENGTH: 28
<212> TYPE: PRT
<213> ORGANISM: Artificial Sequence
<220> FEATURE:
<223> OTHER INFORMATION: VIP variant 5

<400> SEQUENCE: 6

His Ser Asp Ala Val Phe Thr Asp Asn Tyr Ala Arg Leu Arg Lys Gln
1               5                   10                  15

Met Ala Val Lys Lys Ala Leu Asn Ser Ile Leu Ala
            20                  25

<210> SEQ ID NO 7
<211> LENGTH: 31
<212> TYPE: PRT
<213> ORGANISM: Artificial Sequence
<220> FEATURE:
```

<223> OTHER INFORMATION: VIP variant 6

<400> SEQUENCE: 7

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Asn Lys Arg Tyr
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: VIP variant 7

<400> SEQUENCE: 8

His Ser Asp Ala Val Phe Thr Asp Asn Tyr Thr Arg Leu Arg Arg Gln
1               5                   10                  15

Leu Ala Val Arg Arg Tyr Leu Asn Ser Ile Leu Asn Gly Arg Arg
            20                  25                  30

<210> SEQ ID NO 9
<211> LENGTH: 23
<212> TYPE: PRT
<213> ORGANISM: Artificial Sequence
<220> FEATURE:
<223> OTHER INFORMATION: VIP variant 8

<400> SEQUENCE: 9

His Ser Asp Ala Val Phe Thr Asp Asn Tyr Thr Arg Leu Arg Arg Gln
1               5                   10                  15

Leu Ala Val Arg Arg Tyr Leu
            20

<210> SEQ ID NO 10
<211> LENGTH: 31
<212> TYPE: DNA
<213> ORGANISM: Lactobacillus paracasei

<400> SEQUENCE: 10
tcgtcacggc gctgcttttt tcatacaaaa t                                   31

<210> SEQ ID NO 11
<211> LENGTH: 500
<212> TYPE: DNA
<213> ORGANISM: Lactobacillus paracasei

<400> SEQUENCE: 11
tccacaatca aggtgcttgg ctttttcgat cgcgaggtca ccatgtacat cagtcgtgag    60
agcattgtgt tgacagtgat cggcatcgtg ttcggctatc tgctcggcaa tttgctgaca   120
gcctacattt tgtatcaagc cgaaactgag gccgtggttt ttccactcac gatcagcatt   180
gtcggctacc tcacggccac gttactcatg ttggccttca ccggcgtcgt cacctggctc   240
acgcatcgtc gactccaacg ggtggacatg gtcgaagccc tgaaatcaaa cgaataacct   300
acaattttgt caggcagcgt cgtcacggcg ctgcttttt catacaaaat tcatcaaaaa   360
ttgggattaa aaacgttcat gatcgcaatt ttgaagcgca aatgaagatt gagaccaact   420
cctaacagtc ctgtaacgct gacgtaacat tgacacagta aagtagcctt tagttaatca   480
aattaagggt gaggtcaaaa                                                500

```
<210> SEQ ID NO 12
<211> LENGTH: 31
<212> TYPE: PRT
<213> ORGANISM: Lactobacillus paracasei

<400> SEQUENCE: 12

Met Lys Phe Asn Lys Val Met Ile Thr Leu Val Ala Ala Val Thr Leu
1               5                   10                  15

Ala Gly Ser Ala Ser Ala Val Thr Pro Val Phe Ala Asp Thr Ser
            20                  25                  30

<210> SEQ ID NO 13
<211> LENGTH: 93
<212> TYPE: DNA
<213> ORGANISM: Lactobacillus paracasei

<400> SEQUENCE: 13
atgaaattca ataaagtcat gatcacgttg gttgctgcag ttaccttagc aggttctgct      60
agcgccgtaa caccagtttt cgctgataca agc                                   93

<210> SEQ ID NO 14
<211> LENGTH: 1347
<212> TYPE: DNA
<213> ORGANISM: Lactobacillus brevis

<400> SEQUENCE: 14
gtgatggata caataataa tcaatttaat aaccaacaac atgatcataa tgaagaaacc        60
acaccaactc cggaaccacg gaaacggcgg ggtggcctga cactgacgaa agtggcagtg      120
acggctgcgg tcgctggact cttaggcggc ggggttgcgt acggcggtat caactacttt      180
aataatagtg ggatgaatga tacggcggtg ccagccggga gtaactcgac cgggaacacc      240
aagacctcta acgtcaacgt caatgtctcg agtcaatcaa ccaaggcctt taataaggtt      300
aaaggggcca tggtctcggt gattaattta cagaaggaaa atagtagtag cgggacgctt      360
ggccaattat tcggctcaag ctcgagctcc aattcatcga aatccaagtc agagctggaa      420
gaagcttccg aaggttctgg ggtgatttat aagaaggacg gtaacgtggc ttacatcgtg      480
acgaacaatc acgtggtttc cggctcttca gccttacgag tcgtgacgag ttccggtaaa      540
caactgcaag cgaagttggt tggtaaggat tccgttaccg acttggccgt cttaaaggtt      600
aacggctcgt cattaaagac cgtggcgtca tttggaaact cagataatat caaggttggg      660
gaaacggcct tggcaattgg ctcaccactg ggcagccaat acgcaacgtc attgacgcaa      720
gggatcatct ccgccaagaa gcggacgatt gaaacgacta attcttcggg aacgcaaacc      780
gggaatgcaa cggttattca gacggatgcg gcgattaacc ctgggaactc aggggggggcc      840 ttgattaatg tcggtggcca agtggtcggc attacctcat cgaagatcgc cagtgatgcg      900
gaaggcacca gcgttgaagg gatgggcttt gccattccat ctaacgaagt ggtcaatatc      960
atcaatcaac tggtcaagaa cgggaaggtc gtgcggccag cgttagggat tacctacgtt     1020
gacttggcga acgtttctag tgcgcaacag aaatcgatcc tgaagttacc atctaatgtg     1080
gaaaacgggg tcgtggtgat gagtgcttcg gcgggctcac cagcgaagaa ggccggcttg     1140
agcaagtatg atgtgattac ggcgctgggc ggtcatcaga tttcagacca atccacgttg     1200
cgagatattt tgtacaagta taagctgaac gataaggtct cgatcactta ctatcacaat     1260
ggtaagaaga agaccagcac cattaaatta acggaaacat cttctcaatt aaagactagc     1320
tcgacgacgg caacgtcaga gagttag                                         1347
```

-continued

<210> SEQ ID NO 15
<211> LENGTH: 2535
<212> TYPE: DNA
<213> ORGANISM: Lactobacillus brevis
<400> SEQUENCE: 15
atgacagaat caacgcactt gtatgacctg ttccacccgg cacactacga tatttatctc        60
gatattaacc gcgaaacgaa gcaaattagc gggaagacga cgattactgg tgatgcctta       120
gccacgacga ttggcattca ccagaagttc ttaaagatcc aacaggtaac ggttgacggc       180
aaagccgtga cggttacgga tgatcctgcg gccgaagcca ttcggattcc ggtcccacag       240
acgggtaacg tgacgttagc cattgattac acggcgccat taactgatag catgatgggg       300
atttacccat cctactacga cgttaacggc gtacaaaagc aaatcattgg aacccagttt       360
gaaacgaccg ctgcgcgcca agctttccca agtatcgatg aaccggaggc caaagcaacc       420
tttgacctag cgattaagtt cgatgaacag cctggtgaaa cggttatcag taacatgcct       480
gagaccaagg tcgaagccgg cgtgcactac tttgacacca cggttaagat gtccacgtac       540
ctgattgcct ttgcctttgg tgatttgcaa agtaagatga cgactactaa gagtgggggtt      600 caggttgggg tgtttgctac caaggcgcat caagccaatg aattggactt tgcgttagac       660
attgccaagc gctcaattga attttacgaa gacttctatc agacaccttca tccactacca       720 cattcctggc agttagcttt acctgactttt tccgctggcg ccatggaaaa ctggggattg      780
gttacttacc gggaagctta cctcgtttta gaccccgaca atacgtcgtt tgaaacgaag       840 caacggggttg ccaccgtcat tgctcatgaa ctggcccacc aatggtttgg tgatttggtt      900
acgatgaagt ggtgggatga tctttggttg aacgaaagtt ttgccaacat gatggaatac       960
gttgctattg atgccatcga acctgactgg cacatttggg aagtcttcca aacaactgaa      1020
gccccgatgg ccttacaacg ggacgcaacg gacggtgtac aatctgtcca cgtgcaagta      1080
gaagatccag ctgaaattga tgcgctcttt gatagtgcca ttgtttacgc caagggtgcc      1140
cggatgttag tcatggtacg ggctttaatt ggcgatgatg ctctgcgaac gggcctgaag      1200
gcttacttcg acgcccataa gtttggtaat gcaactgggg ctgacttgtg gtctgcttta      1260
gggactgctg ccaatatgga tttgaagagc gtaatgaatt cgtggctgga acaacctggt      1320
tacccagtct taacggctgc ggtggtcgat ggtcagttga cagtgaccca gcaacaattc      1380
tttattggcg atggcacaga cgccaaacgt caatggcaag tgccattgag cagtaactat      1440
gctgaagtcc cagaattgtt gacggcgcca caagtgacgt taggaactta tgcggattta      1500
cggcaggcta atggacagcc gttccggcta aatgtcggca taattcaca tgcgattgtg       1560 aagtacgatg ataccttact agcagatatt ttagatcaca tcactgagtt aacagcgatt      1620
gatcaactcc aattgctaca agatcaacga ctactggctg aagggcggca gatttcttat      1680
gcggatgtcg tcgccttgtt gccacgattt gcggctagtg aagctacggt ggttaacgat      1740
gcgttgtatc aggtcgctgg taacttgaag aagttcgtca cgccagattc tgatgccgaa      1800
aagcaactgc aacaattctt tgatcggtta agtgcggcac aagttgaccg gttggggtgg      1860 accctaaag ctggcgaatc taatgatgac cagttaaccc ggccatatgt attaagcgcg       1920
gccctctatg ctaaaaatgc ccaatcagtc gccgctgcgc atgaactgtt cacagccaat      1980
cgcgacaatt tagcaggctt gccagctgca acgcgttact atgttttggc aaatgaagtc      2040
acgaacttca gtgacgcaac ggtctttgat cagttgctga cagattaccg gcaagcaacg      2100
gatgccagct acaaggccga tctgtgtgcc gcattgacga ccacaccaga tgccaagttg      2160

-continued

```
attgcgaagt taatcgcagt ctttgaaaac gcggccacgg ttaaaccaca ggacttacgg    2220
gcttggtacc gtggtgtctt ggccaatgcc aaggggcagc aggtggcttg ggactggatc    2280
cgtcaagatt gggattggtt ggaagcaact gtgggtggtg atatggaatt caccacattt    2340
attacggtaa ctgcggcgat cttccacaca cctgaacggt tagctgagtt caaggaattc    2400
tttgaaccaa agattccgac gcctggttta ggacgtgaaa tcaagatgga taccaaggtt    2460
atcgcaagtc gcgtggcctt agttgaagat gaaaaagccg cagtgaatgc tgcggtggca    2520
caagtcgtcc aataa                                                     2535

<210> SEQ ID NO 16
<211> LENGTH: 597
<212> TYPE: DNA
<213> ORGANISM: Lactobacillus brevis

<400> SEQUENCE: 16
atgaatttag taccaacagt tattgaacaa tcatcccgtg gcgaacgggc ctatgatatt      60
tattcacgac tattaaaaga ccggattatc atgttatctg gtccaattga agatgacatg     120
gccaacgcca tcatcgcgca gttactcttc ttggatgccc aagactcaac caaggacatt     180
tcactctaca tcaactcacc tggtggtgtc gtttcttccg gcttggccat ctatgatacc     240
atgaacttca tccaatctga cgtgcaaacg atcacgttag ggatggcagc ttccatggca     300
agtgtcttgg cttcatctgg gactaagggc aagcgttttg ctttgcctca cgcccaagtg     360
atgattcacc aaccatctgg tggtgcccaa ggacaacaaa cggaaatcga aattgctgct     420
cgtgaaatct tgaagacccg tgaattgatc aacaagattt tagcagagaa ttccggtcaa     480
ccgattgaac gcctcaatca agatactgaa cgagacaact acttgagtgc tcaagaagcg     540
gttgattatg gattaattga ccacatcatg accaacagta gtgaacaaaa gaagtaa       597

<210> SEQ ID NO 17
<211> LENGTH: 1050
<212> TYPE: DNA
<213> ORGANISM: Lactobacillus brevis

<400> SEQUENCE: 17
gtgtggaatt taacgcgacg gcagtggcgg cagattctag taacggtgat attagcactt      60
gcagtgttgc tattttttct gtggccattg cccaagtata ttgagggtcc cggtgaggca     120
gacaatttga aatcatttgt cacagttgcc caacatcccg ataagcataa gggaaaatat     180
atgattacct cagttgcgtt ggcgcaagct cgtccagttt cctacctcta tgccaaattt     240
aatccctatt acagcattga gagtgtagcg tcagtgacgg gtggcgagag taatgcgacc     300
tatgataaag ttcagaactt ttatatgaaa agcgccatca atgagtcgat ttataccgca     360
tatcgggcgg cccataaaac ggtgaagcgt cattatttgg gaatttacgt tttgagtgtt     420
gatcgtcggt caccctttgc ccaagcgtta aaggtgggcg atacggtgac ggaggtaaat     480
ggtcatcatt tcaactctat gacggggtat caacgatata tccagcgaca aaaagtggga     540
caacggacga ccattacgta tcagcacaat ggtaaaacac accacgtaac tgccaaattg     600
atgcggttgc caacgaaaaa agcgggtatt gggattactt tgacggataa cgtcaaagtt     660
agtgctcggc ctaaagtgca ggtgaatccc ggcaacatcg gtggtccgtc aggtggttta     720
atgtttagct tacagattta tacgcaagtg acggggcagg acttacgtca cgggcgaaag     780
attgcaggaa ccggaacggt tgatggtgac ggcaacgttg gcgagattgg tggtattgat     840
```

-continued

```
aagaaaatta tcgctgctaa gcgcgcaggg gcgacggtct tctttgctcc ctacgtgaaa        900
ccgacaaaat tgttactgaa gtatgaagaa caacaccaaa cgaattatca attggctaag        960
gcaacagcga aaagtatgc gccgaatatg aaagttgtgc cagtaaaatc gtttgacgat        1020
gcagttcatt acttaaggac acaccgttaa                                        1050

<210> SEQ ID NO 18
<211> LENGTH: 606
<212> TYPE: DNA
<213> ORGANISM: Lactobacillus brevis

<400> SEQUENCE: 18
atgttcacag gaataattac agatcaaggt tacattcgac aaataaataa aacagccacg         60
ggagcacagc tcgttattca aacgacacgg gctcatcaga cacgcacgt cggggacagc        120 atcgccgtga acgggatctg cctcacttta accgcagtga ctgacgaagc atttaccgtt        180
gttgcaatgg ctgaaacctt gcagcgtacg acactgggaa cttggcagac tggtatgcag        240
gtcaatctgg aagctgcttt acgagcagat caaggattgg atggacatat cgttcagggg        300
cacgttgaca ccacagcgac cttacgagca agtcataccg aaggggccgc agtccggttg        360
acctttgatg tatcagctga tcaagctcct tacttggttg aaaagggtgc tgtggccttg        420
gatggtgtta gtttaacggt cacggcagtt actcgtcaga cggttcaggt agcgctgatt        480
ccctatacgt tggcacatac gagtcttggt catctacagt gcggtgatca ggtgaatgta        540
gagacagata ttttggggaa gtacgtggtt cgtcagtacc agttaggggg gatgactgat        600
gactag                                                                  606

<210> SEQ ID NO 19
<211> LENGTH: 951
<212> TYPE: DNA
<213> ORGANISM: Lactobacillus brevis

<400> SEQUENCE: 19
gatttgccgg tgtccccgga attagcgacc aagtcccagt ataggcagt ggaattacag         60 tgagtagagt attagcttct atgagctgaa tagtcctaaa ttggtgttga caccgcgtcg        120
tacaccacag gcgcgatcga cccaaaacta aacgagttgc actaatgaca tttacacgcg        180
cagtgggtcg catacctgct ttagcgggtg gagattcggg tgaaggaatc gttagtcgct        240
acagttgtta cgcatcgacc gttataactt cccgtgtgga tccttctata gtcgtgaaga        300
gaccatttcg actgtcgaat taaacggtag taactgcatt ttaactttct cgcacaccgt        360
tccaccgttt cggtaactac cgtgtagtcg gcctaaggtg cgactttgct agtaggcggc        420
tctcagaccc acgcaggcgt tgcagagtta gtgtaaccgg tcaactagtt accaaagtgg        480
aactactgga acggttcggg cggtgactga tggtatttga tctgggttta gtggtttcac        540
cagtggtttt cgaactaggc aatgctaagc tagtgtttta cggaaaaaaa gacgaactat        600
aacgactaat ttcagacgta ggtggttcct tgccgctggt ttcagccagt atagaccggg        660
cactataagc cctgatagtt gcatcgcaac tttccgggtg agcagggttt ataccaacac        720
cacaacgtta ttttttggctt ataatcatag gggtgcttcc ttggtgttct caagcctaaa        780
ttactctggt ttcccgtgga aaaatcatca gttatcaccc ttcgggagaa cgtttaattt        840
ggcgtaaacc atcggtttat tcgattagca aggccaaggg catgccaggc aaaaaagcac        900
tgggcagcag ttctgtcaga atcgatttag atttatacgg agaagattgt g                951
```

<210> SEQ ID NO 20
<211> LENGTH: 1818
<212> TYPE: DNA
<213> ORGANISM: Lactobacillus brevis

<400> SEQUENCE: 20

```
atgtgtggaa ttgttggagt gacgggtaac gataacgccg ttaaaatttt agttaatggg      60
ctacaaaagt tggaatatcg cggctatgat tcagccggaa tctatgttaa tgaccaaaaa     120
ggccaggatt atttggtaaa ggccaagggc cggatttccg aattaagtgc taagattacg     180
ccagaagttc acggatcaac tgggattggt catacgcgtt gggcaacgca tggggtggtt     240
agcgtggata atgcgcaccc acatttctcc aacgacgacc gcttttactt ggttcacaat     300
ggtgtgattg ataacttcca agaacttaag gcgcaatatt taagtgatgt acctttccgg     360
agccaaacgg atacagaagt tgtcgtacag ttgattgata agtttgcggt agaagatcac     420
ttagatgcta agcaggcttt cttgaagaca ctaggcctgc tgaagggttc ctcatatgcc     480
ttcttaatga tggatcggga acaaccagac acattatttg tggctaagaa caagagcccc     540
ttattaattg gtgtcggcga tggcttcaac gttgtctgct cagatgcctt ggccatgtta     600
cgggaaaccc acgatttctt ggaattaatg gatggtgaag ttgtaacgat cacgccagat     660
aaagtggcaa tcgaagacgc tgatggtcag actgttgagc ggaaaccttt ccacgttgac     720
atgaacgctg atgaagcaga caagggcact tatccattct acatgttaaa agaagttgat     780
gaacaaccta acgtgatgcg taaattagcc caaacatatc tgtcagaaca cggcgaacct     840
aacattgaca agcaattgct acaagcaatg gaagccgctg atcgattgta tatcattggc     900
gctgggacga gttaccacgc tgggctgatt ggtaagcgcc tctttgaaaa cttggctcac     960
attccaacgg aagttcatgt gtcatcagaa tttgcgtatg aacaaccgat gttatctgag    1020
aagccattct ttattttcct gacccaatct ggagaaacag ctgatagtcg tgaagttttg    1080
gttaacgtga acgatgcggg ttacccaagc ttgacaatca ccaatgtgca aaactccacg    1140
ttatcacgtg aagccactta caccttgttg ttacatgccg gtccagaaat tgcggtggct    1200
tcaaccaagg cgtacacggc ccaaattgct ttggaagcta tcttggccaa ggctttaggt    1260
gaattaactg gccagattat tgcgcagaat ttcaatattc ggcaacagtt gggactcgtc    1320
gcaactggga tgcaagccat tgtggatgaa aaggataagc tggaagaaat gtcttccaag    1380
tacttgttaa agactaaccg ggcgtttttac attggccggg ggatcgacca cgccgtttcc    1440
ttagaagcag ctttgaaact gaaagagatt tcttatattc agtgtgaagg cttcgcgtct    1500
ggtgaattaa agcatggcac gattgcatta attgaggctg gaacaccagt tattgggttt    1560
attacgcagg cgaagacggc tggtttaacc cggagtaact tacaagaaac gatggcccgt    1620
ggtgcacaaa cattgacgat tgtccgggaa agtttagccg tagatggtga tgacttagtc    1680
ttaccggatg tcgatgagat gttaatgcca ctcttaagtg ttgtaccagc acaattgttg    1740
gcctactaca cgagtttaaa taagggctta gatgttgata agccacggaa cttggccaag    1800
agtgtgacag ttgaataa                                                   1818
```

<210> SEQ ID NO 21
<211> LENGTH: 18
<212> TYPE: DNA
<213> ORGANISM: Artificial Sequence
<220> FEATURE:
<223> OTHER INFORMATION: primer

<400> SEQUENCE: 21 agcaacctttt gacctagc                                              18

<210> SEQ ID NO 22
<211> LENGTH: 20
<212> TYPE: DNA
<213> ORGANISM: Artificial Sequenc
<220> FEATURE:
<223> OTHER INFORMATION: primer

<400> SEQUENCE: 22
aattccatat caccacccac                                            20

<210> SEQ ID NO 23
<211> LENGTH: 17
<212> TYPE: DNA
<213> ORGANISM: Artificial Sequence
<220> FEATURE:
<223> OTHER INFORMATION: primer

<400> SEQUENCE: 23
cccgatggcc ttacaac                                               17

<210> SEQ ID NO 24
<211> LENGTH: 18
<212> TYPE: DNA
<213> ORGANISM: Artificial Sequence
<220> FEATURE:
<223> OTHER INFORMATION: primer

<400> SEQUENCE: 24
ggaacggctg tccattag                                              18

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ctaaatgagg agggttcgcg                                            20

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
aagctggcgc tttcattcc                                             19

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27
acctctaacg tcaacgtc                                              18

-continued

```
<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
agttcccagg gttaatcg                                                  18

<210> SEQ ID NO 29
<211> LENGTH: 17
<212> TYPE: DNA
<213> ORGANISM: Artificial Sequence
<220> FEATURE:
<223> OTHER INFORMATION: primer

<400> SEQUENCE: 29
taaccgcagt gactgac                                                   17

<210> SEQ ID NO 30
<211> LENGTH: 19
<212> TYPE: DNA
<213> ORGANISM: Artificial Sequence
<220> FEATURE:
<223> OTHER INFORMATION: primer

<400> SEQUENCE: 30
agctgataca tcaaaggtc                                                 19

<210> SEQ ID NO 31
<211> LENGTH: 17
<212> TYPE: DNA
<213> ORGANISM: Artificial Sequence
<220> FEATURE:
<223> OTHER INFORMATION: primer

<400> SEQUENCE: 31
agcattgtgt tatcagc                                                   17

<210> SEQ ID NO 32
<211> LENGTH: 17
<212> TYPE: DNA
<213> ORGANISM: Artificial Sequence
<220> FEATURE:
<223> OTHER INFORMATION: primer

<400> SEQUENCE: 32
gcagcattgg tagcaac                                                   17

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
gtgtggcaag gtggcaaagc ca                                             22

<210> SEQ ID NO 34
<211> LENGTH: 25
<212> TYPE: DNA
<213> ORGANISM: Artificial Sequence
<220> FEATURE:
```

-continued

```
<223> OTHER INFORMATION: primer

<400> SEQUENCE: 34
ccgatctaca ggcccaactc gatga                                                     25
```

MICROORGANISM EXPRESSING VASOACTIVE INTESTINAL PEPTIDE, AND USE THEREOF

CROSS-REFERENCE TO RELATED APPLICATIONS

This application is a National Stage application of PCT/KR2021/004479, filed Apr. 4, 2021, which claims priority to and the benefit of Korean Patent Application No. 10-2020-0047660 filed on Apr. 20, 2020, both of which are hereby incorporated by reference in their entirety.

INCORPORATION OF ELECTRONICALLY-FILED MATERIAL

The instant application contains a Sequence Listing which has been submitted electronically in ASCII format and is hereby incorporated by reference in its entirety. Said ASCII copy, created on May 31, 2023, is named "96M4345.TXT" and is 19,995 bytes in size.

TECHNICAL FIELD

The present disclosure relates to a microorganism expressing vasoactive intestinal peptide (VIP), and a composition including the microorganism, for preventing or treating a disease causing damage to the gastrointestinal tract.

BACKGROUND ART

VIP is a vasoactive intestinal peptide hormone. VIP is a peptide with 28 amino acid residues belonging to the glucagon/secretin superfamily, and is a ligand of class II G protein-coupled receptors.

Korean Patent Publication No. 2014-0000620 discloses *Lactobacillus* that increases VIP levels in the enteric nervous system and its use for treating irritable bowel syndrome (IBD). The microorganism is a strain screened from nature and is not a recombinant microorganism.

Chinese Patent Publication No. 108753670 discloses a recombinant microorganism *Lactococcus lactis* NZ9000 that expresses VIP and has abundant selenium nanoparticles (SeNP) in the cells. It is described that when this recombinant microorganism is used as a selenium additive, the issues of selenium's strong toxicity, low bioavailability, high potential to cause environmental pollution, and high production costs may be solved because selenium is present in the cells in the form of nanoparticles, and at the same time, an issue of residual antibiotics may be solved because the microorganism secretes VIP, an antibacterial peptide. In addition, the pNZ8148 plasmid of the NICER *Lactococcus lactis* expression system was used for VIP secretion expression.

However, a recombinant microorganism of the genus *Lactobacillus* expressing exogenous VIP, recombinant lactic acid bacteria expressing exogenous VIP under a constitutive promoter, and the use of such a microorganism in humans to prevent or treat a disease causing damage to the gastrointestinal tract, such as IBD, are not known.

DESCRIPTION OF EMBODIMENTS

Technical Problem

A purpose of the present disclosure is to provide a recombinant microorganism of the genus *Lactobacillus* expressing exogenous VIP.

Another purpose is to provide recombinant lactic acid bacteria expressing exogenous VIP under a constitutive promoter.

Still another purpose is to provide a composition including the microorganism for preventing or treating a disease causing damage to the gastrointestinal tract in humans.

Solution to Problem

An aspect of the present disclosure provides a recombinant microorganism of the genus *Lactobacillus*, in which a promoter and an exogenous gene are introduced, and a protease is inactivated, wherein the exogenous gene is operably linked to the promoter and encodes vasoactive intestinal peptide (VIP).

Another aspect of the present disclosure provides a recombinant microorganism which is a lactic acid bacterium, in which a constitutive promoter and an exogenous gene are introduced, and a protease is inactivated, wherein the exogenous gene is operably linked to the promoter and encodes vasoactive intestinal peptide (VIP).

Still another aspect of the present disclosure provides a composition for preventing or treating a disease causing damage to the gastrointestinal tract in humans, including a recombinant microorganism, which is a lactic acid bacterium, in which a promoter and an exogenous gene are introduced, and a protease is inactivated, wherein the exogenous gene is operably linked to the promoter and encodes vasoactive intestinal peptide (VIP).

Hereinafter, the disclosure will be described in detail.

The term "VIP" or "VIP protein" or "VIP polypeptide" used herein refers to a biologically active polypeptide having one or more of the biological activities described herein.

In humans, the q25 region of chromosome 6 in the human genome encodes a member of the secretin family that is 170 amino acids in length. This member of 170 amino acids in length is post-translationally truncated to form vasoactive intestinal peptide (VIP). The active form of the VIP polypeptide functions to lower blood pressure, increase vasodilation of blood vessel walls, relax smooth muscle in the tissues of the respiratory system and gastrointestinal tract, decrease the immune response through the promotion of Th2 as well as reduction of the Th1 response, regulate the innate and acquired immune response, or promote the secretion of electrolytes in the intestine. It has also been shown that VIP is active in the central nervous system as a neurotransmitter and in communication with lymphocytes. The bioactivity of VIP is transmitted through three known receptors: $VIP_1R$, $VIP_2R$, and $PAC_1R$. These receptors are known to cause CAMP enrichment as well as production of intracellular calcium. Like VIP, the affinity of the receptors for secretins depends on the subtype and the amino acid sequence of the ligand. Human natural VIP has a short half-life, of about 2 minutes in the bloodstream.

VIP referred to herein includes a variant that mimics the function of natural VIP. The variant includes one having an increased half-life than natural VIP and equivalent or greater bioactivity than natural VIP.

As used herein, VIP includes, but is not limited to, human VIP, recombinant human VIP, rat VIP, and/or recombinant mouse VIP. VIP may be one having 50% or more, 60% or more, 70% or more, 85% or more, 90% or more, 95% or more, 98% or more, 99% or more, or 100% sequence identity with the amino acid sequence of SEQ ID NO: 1. VIP may each have the amino acid sequence of SEQ ID NO: 1, 2, 3, 4, 5, 6, 7, 8, or 9. VIP of SEQ ID NO: 1 is human-derived natural VIP. VIP having the amino acid sequence of SEQ ID NO: 2, 3, 4, 5, 6, 7, 8, and 9 are respectively, VIP1, VIP2, VIP3, VIP4, VIP5, VIP6, VIP7, and VIP8, VIP variants of human-derived natural VIP.

The VIP polypeptides used herein may be isolated from a variety of sources, such as human tissue or other sources, or prepared by recombinant or synthetic methods.

The term "VIP polypeptide" also includes variants of VIP polypeptides. Herein, VIP may be modified in such a way that a chimeric molecule is formed including VIP fused to another heterologous polypeptide or amino acid sequence.

As used herein, "protease" is a generic term for enzymes that degrade proteins, and may include any type known in the art without particular limitation.

In the present specification, "auxotroph" refers to a strain that cannot grow in a synthetic medium consisting only of inorganic salts and a carbon source and grows only when one or more nutrients are supplemented, and any known kind in the art may be included without particular limitation.

The microorganism according to an aspect of the present disclosure is a recombinant microorganism, which is of the genus *Lactobacillus*, in which a constitutive promoter and an exogenous gene are introduced and a protease is inactivated, wherein the exogenous gene is operably linked to the promoter and encodes vasoactive intestinal peptide (VIP).

The microorganism according to another aspect of the present disclosure is a recombinant microorganism, which is a lactic acid bacterium, in which a promoter and an exogenous gene are introduced and a protease is inactivated, wherein the exogenous gene is operably linked to the promoter and encodes vasoactive intestinal peptide (VIP).

The lactic acid bacterium may belong to the genus of *Lactobacillus, Lactococcus, Bifidobacteria, Streptococcus, Leuconostoc, Weissella, Pediococcus,* or *Enterococcus,* in particular, to the genus of *Lactobacillus* or *Lactococcus,* and may be, for example, *Lactobacillus paracasei, Lactobacillus brevis, Lactobacillus plantarum* or *Lactococcus lactis.*

The microorganism of the genus *Lactobacillus* may be *Lactobacillus paracasei, Lactobacillus brevis,* or *Lactobacillus plantarum.* For example, the microorganism may be *Lactobacillus plantarum* LMT1-9 (KCTC 13421BP), *Lactobacillus paracasei* LMT1-21 (KCTC 13422BP), or *Lactobacillus brevis* LMT1-46 (KCTC 13423BP).

The promoter may be a constitutive promoter. The promoter may have transcription initiation efficiency in lactic acid bacteria equal to or greater than that of a promoter in the art, for example, the P11 promoter. The promoter may also be an inducible promoter. The inducible promoter may be, for example, a Nisin inducible promoter. The promoter may be PR4 derived from *Lactobacillus paracasei* including the polynucleotide of SEQ ID NO: 10. PR4 may consist of the nucleotide sequence of SEQ ID NO: 11.

The microorganism according to the present disclosure is characterized by having an exogenous gene encoding VIP introduced. The introduction may be by transformation, transduction, transfection or electroporation. The introduced exogenous gene may be integrated into the genome of the host cell or may exist without being integrated. For example, the exogenous gene may be integrated into the genome of the host cell.

In addition, the microorganism according to the present disclosure is characterized by having a protease inactivated. In an embodiment, the gene encoding a protease may be deleted. "Deletion" includes deletion of at least a portion, for example, all or part of a gene.

According to an embodiment, the gene encoding a protease is replaced with an exogenous gene, which is operably linked to a promoter and encodes vasoactive intestinal peptide (VIP), whereby the introduction of the exogenous gene and deletion of the protease gene may be implemented simultaneously. "Replacement" includes replacement of at least a portion, for example, all or part of a gene.

In the present specification, "protease" may include any type known in the art without particular limitation. For example, the protease may be at least one selected from the group consisting of high temperature requirement A (HtrA), Aminopeptidase N (PepN), Caseinolytic protease P (ClpP) and Lon protease (Lon), and may be, for example, HtrA and/or PepN, or for example, HtrA. The htrA gene may be a *L. brevis* htrA gene, particularly, the gene of SEQ ID NO: 14. The pepN gene may be a *L. brevis* pepN gene, particularly, the gene of SEQ ID NO: 15. The clpP gene may be a *L. brevis* clpP gene, particularly, the gene of SEQ ID NO: 16. The lon gene may be a *L. brevis* lon gene, particularly, the gene of SEQ ID NO: 17. In these microorganisms, the yield or productivity of the VIP protein may be increased by preventing the exogenous VIP protein from being degraded because the protease is not expressed. According to an embodiment, when HtrA is not expressed, it is possible to significantly increase the productivity of the VIP protein.

The recombinant microorganism may further include a signal sequence operably linked between the promoter and the exogenous gene. When the signal sequence is linked in frame with the exogenous protein gene, the ability to secrete the exogenous protein out of the cell may be greater than that of a signal sequence in the art, for example, a USP45 signal sequence. The signal sequence may be one encoding SP4 (SEQ ID NO: 12) derived from *Lactobacillus paracasei.* For example, SP4 may have the nucleotide sequence of SEQ ID NO: 13. The microorganism may secrete VIP out of the cell.

In an embodiment, the recombinant microorganism may be an auxotroph. The auxotroph may be, for example, one in which is deleted at least one gene selected from the group consisting of riboflavin biosynthesis protein gene (ribB), thymidylate synthase gene (thyA) and glutamine-fructose-6-phosphate aminotransferase gene (glmS), for example, ribB and/or thyA, for example, ribB, but is not particularly limited thereto. ribB may be *L. brevis* ribB, in particular of SEQ ID NO: 18. thyA may be *L. brevis* thyA, particularly of SEQ ID NO: 19. glmS may be *L. brevis* glmS, in particular of SEQ ID NO: 20. In this case, environmental safety may be enhanced by controlling the growth and survival of the recombinant microorganisms. "Deletion" includes deletion of at least a portion, for example, all or part of a gene.

Another aspect of the present disclosure provides a composition including the above-mentioned microorganism, for use in preventing or treating a disease causing damage to the gastrointestinal tract.

The disease may be one that causes inflammation of the gastrointestinal tract. The disease may be at least one selected from the group consisting of inflammatory bowel disease (IBD) and colitis. The inflammatory bowel disease may be ulcerative colitis or Crohn's disease.

The composition may include a pharmaceutically acceptable or sitologically acceptable carrier, excipient or diluent. The pharmaceutically acceptable or sitologically acceptable carrier may be any standard pharmaceutically acceptable or sitologically acceptable carrier such as a phosphate buffered saline solution, 5% aqueous solution of dextrose and an emulsion (for example, oil/water or water/oil emulsion). Non-limiting examples of excipients include adjuvants, binders, fillers, diluents, disintegrants, emulsifiers, wetting agents, lubricants, glidants, sweetening agents, flavoring and coloring agents. The preferred pharmaceutically or sitologically acceptable carrier depends on the intended mode of administration of the active agent. Typical modes of administration include enteral (for example, oral) administration. The composition may be in a unit dosage formulation. The composition may have an oral dosage formulation. The composition may be a food or a pharmaceutical composition. The composition may include dry matter of the microorganism. The composition may include a medium of the microorganism.

As used herein, "pharmaceutically acceptable or sitologically acceptable" refers to one substantially not causing adverse reactions when administered to a subject. The adverse reaction may be toxicity, allergy, or an immune response.

Another aspect provides a kit for use in preventing or treating a disease causing damage to the gastrointestinal tract, including the above recombinant microorganism and another drug for treating a disease damaging the gastrointestinal tract. The recombinant microorganism is as described above. The recombinant microorganism may be in the form of the composition described above. The kit may include instructions for using the recombinant microorganism and the other drug for treating the disease causing damage to the gastrointestinal tract to prevent or treat the disease causing damage to the gastrointestinal tract.

The other drug for treating a disease damaging the gastrointestinal tract includes any drug that treats a disease damaging the gastrointestinal tract, for example, inflammatory bowel disease. Drugs for treating a disease damaging the gastrointestinal tract may include the following drugs:

(i) Steroidal Anti-Inflammatory Agents

Dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol, paramethasone acetate, fludrocortisone acetate, clobetasol propionate, diflorasone acetate, dexamethasone propionate, difluprednate, betamethasone dipropionate, budesonide, diflucortolone valerate, amcinonide, halcinonide, mometasone furoate, hydrocortisone butyrate propionate, flumetasone pivalate, clobetasone butyrate, dexametasona acetate, etc.

(ii) 5-aminosalicylic Acid

Sulfasalazine, mesalazine, olsalazine, balsalazide, etc.

(iii) Immunomodulators or Immunosuppressants

Methotrexate, cyclophosphamide, MX-68, atiprimod dihydrochloride, BMS-188667, CKD-461, rimexolone, cyclosporine, tacrolimus, gusperimus, azathiopurine, anti-lymphocyte serum, freeze-dried sulfonated normal immunoglobulin, erythropoietin, colony stimulating factor, interleukin, interferon, etc.

(iv) JAK Inhibitors

Tofacitinib, ruxolitinib, etc.

(v) TNF Inhibitors

Recombinant TNF-alpha-receptor IgG-Fc fusion protein (etanercept), infliximab, adalimumab, certolizumab pegol, golimumab, PASSTNF-α, soluble TNF-α receptor, TNF-α binding protein, anti-TNF-α antibody, CDP571, etc.

(vi) Integrin Inhibitors

Natalizumab, vedolizumab, AJM300, TRK-170, E-6007, etc.

(vii) Interleukin-12/23 Inhibitors

Ustekinumab, briakinumab (anti-interleukin-12/23 antibody), etc.

(viii) Non-Steroidal Anti-Inflammatory Drugs (NSAIDs)

(a) Classical NSAIDs

Alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, ketophenylbutazone, loxoprofen sodium, phenylbutazone, indomethacin, ibuprofen, ketoprofen, naproxen, oxaprozin, flurbiprofen, fenbufen, pranoprofen, floctafenine, piroxicam, tenoxicam, epirizole, tiaramide hydrochloride, zaltoprofen, gabexate mesylate, camostat mesylate, ulinastatin, colchicine, probenecid, sulfinpyrazone, bucolome, benzbromarone, allopurinol, sodium aurothiomalate, hyaluronate sodium, sodium salicylate, salicylic acid, atropine, scopolamine, levorphanol, oxymorphone, a salt thereof, etc.

(b) Cyclooxygenase Inhibitors (COX-1 Selective Inhibitors, COX-2 Selective Inhibitors, Etc.)

Salicylic acid derivatives (for example, celecoxib, aspirin), etoricoxib, valdecoxib, diclofenac sodium, indomethacin, loxoprofen, etc.

(c) Nitric Oxide-Releasing NSAID.

The description of the microorganism is also applicable to the composition.

Another aspect provides a method of preventing or treating a disease causing damage to the gastrointestinal tract, including administering to the subject the microorganism of an amount that is effective for preventing or treating the disease causing damage to the gastrointestinal tract.

The method may further include administering to the subject a TNF-alpha blocker of an amount effective to prevent or treat a disease causing damage to the gastrointestinal tract. The administration of the TNF-alpha blocker to the subject may be performed simultaneously, before, or after the administering of the microorganism to the subject. The TNF-alpha blocker may be administered via a route the same with or different from the route through which the microorganism is administered. For example, the TNF-alpha blocker may be administered orally or parenterally. The parenteral route may be an injection such as vascular injection, intraperitoneal injection, or subcutaneous injection. For example, the TNF-alpha blocker may be administered intraperitoneally, and the microorganism may be administered orally. The TNF-alpha blocker may be administered intraperitoneally after the microorganism is orally administered. The TNF-alpha blocker may be administered in an amount of 5 mg to 100 mg, 5 mg to 50 mg, 5 mg to 40 mg, 10 mg to 50 mg, or 20 mg to 50 mg per administration.

In the method, the disease may be one causing inflammation of the gastrointestinal tract. The disease may be at least one selected from the group consisting of inflammatory intestinal disease, autoimmune disease, damage of the gastrointestinal tract by radiation or graft versus host disease (GVHD), inflammatory bowel disease (IBD), and colitis including chronic colitis. The inflammatory bowel disease may be ulcerative colitis or Crohn's disease.

As used herein, the "administering" or "administration" refers to acts of giving the microorganism, a composition including the same, or a therapeutic treatment to a physiological system (an organism, in vivo, in vitro, or ex vivo cells, a tissue or an organ). Accordingly, in the method, the microorganism may be in a form of the composition described above. An acceptable route of administration to the human body may be oral, or mucosal (for example, intestinal mucosa, oral mucosa or buccal). The administration may be in combination with an administration of an additional therapeutic agent. The combined administration includes any of simultaneous and sequential administrations.

As used herein, the term "treatment" refers to prophylactic treatment or therapeutic treatment. In certain embodiments, "treatment" refers to administration of microorganisms or a composition to a subject for therapeutic or prophylactic purposes.

A "therapeutic" treatment is a treatment administered to a subject exhibiting pathological signs or symptoms to reduce or eliminate the signs or symptoms. Signs or symptoms may be biochemical, cellular, histological, functional or physical, subjective or objective.

A "prophylactic" treatment is a treatment administered to a subject that does not show signs of a disease or only shows early signs of a disease in order to reduce the risk of developing a pathology. The microorganism or composition described herein may be provided as a prophylactic treatment to reduce the likelihood of developing a pathology, or to minimize the severity of the pathology when it does occur.

As used herein, "therapeutically effective amount" refers to an amount sufficient to carry out the stated purpose. An effective amount may be determined empirically. An effective amount may be determined, for example, depending on the extent to which the microorganism secretes VIP out of the cell. For example, for a person having a body weight of 60 kg, an effective amount may be the number of the microorganisms capable of secreting 0.01 to 300 mg, or 0.5 to 100 mg of VIP per day. For example, an effective amount may be $1 \times 10^5$ cfu to $1 \times 10^{13}$ cfu, $1 \times 10^6$ cfu to $1 \times 10^{13}$ cfu, $1 \times 10^7$ cfu to $1 \times 10^{13}$ cfu, $1 \times 10^7$ cfu to $1 \times 10^{12}$ cfu, $1 \times 10^7$ cfu to $1 \times 10^{11}$ cfu, $1 \times 10^7$ cfu to $1 \times 10^{10}$ cfu, $1 \times 10^8$ cfu to $1 \times 10^{11}$ cfu, $1 \times 10^8$ cfu to $1 \times 10^{10}$ cfu, $2.5 \times 10^8$ cfu to $7.5 \times 10^9$ cfu, $5.0 \times 10^8$ cfu to $5.0 \times 10^9$ cfu, $7.5 \times 10^8$ cfu to $2.5 \times 10^9$ cfu, or about $1 \times 10^9$ cfu per administration.

In the method, the subject may be a mammal. The mammal may be a human, horse, pig, cow, dog, cat, monkey, chimpanzee, sheep, or goat.

The description of the microorganism and/or composition is also applicable to the method.

Advantageous Effects of Disclosure

The recombinant microorganism according to the present disclosure not only is able to produce and secrete VIP with higher productivity, but also exhibits high environmental safety, thereby more effectively prevents or treats a disease causing damage to the gastrointestinal tract.

BEST MODE

Hereinafter, the disclosure will be described in more detail through examples. However, these examples are for illustrative purposes only, and the scope of the present disclosure is not limited in any way by these examples.

Example 1: Preparation of Recombinant Microorganism

A recombinant microorganism expressing exogenous VIP was prepared, according to the homologous recombination genetic engineering method commonly used for lactic acid bacteria (Zhang et al., D-Ala-D-Ala ligase as a broad host-range counterselection marker in vancomycin resistant lactic acid bacteria, J. Bacteriol., 2018), using *Lactobacillus brevis* LMT1-46 (KCTC 13423BP).

Figure 1A:
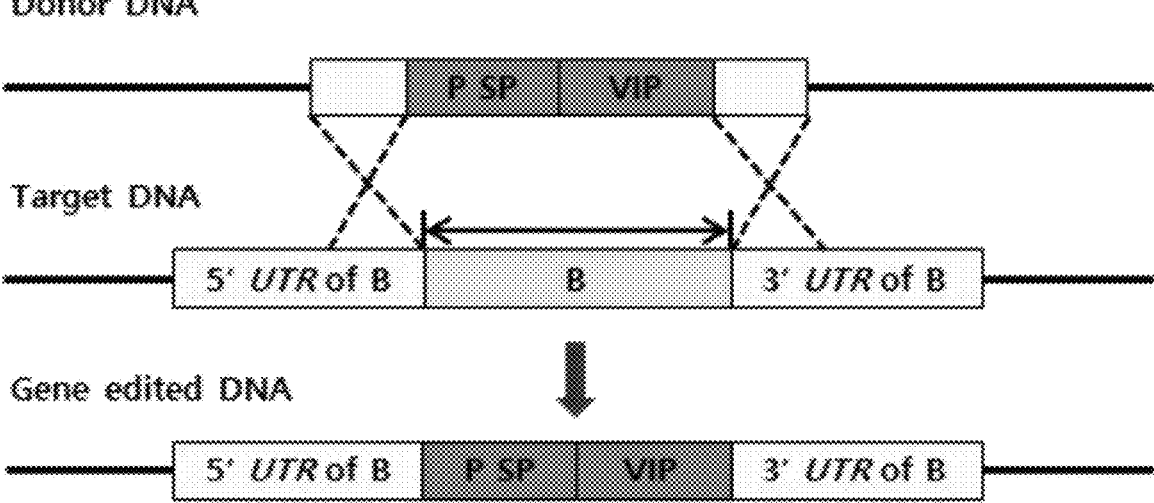
FIGS. 1A and 1B are schematics showing genetically engineered sites of recombinant microorganisms according to an example.
Figure 1B:
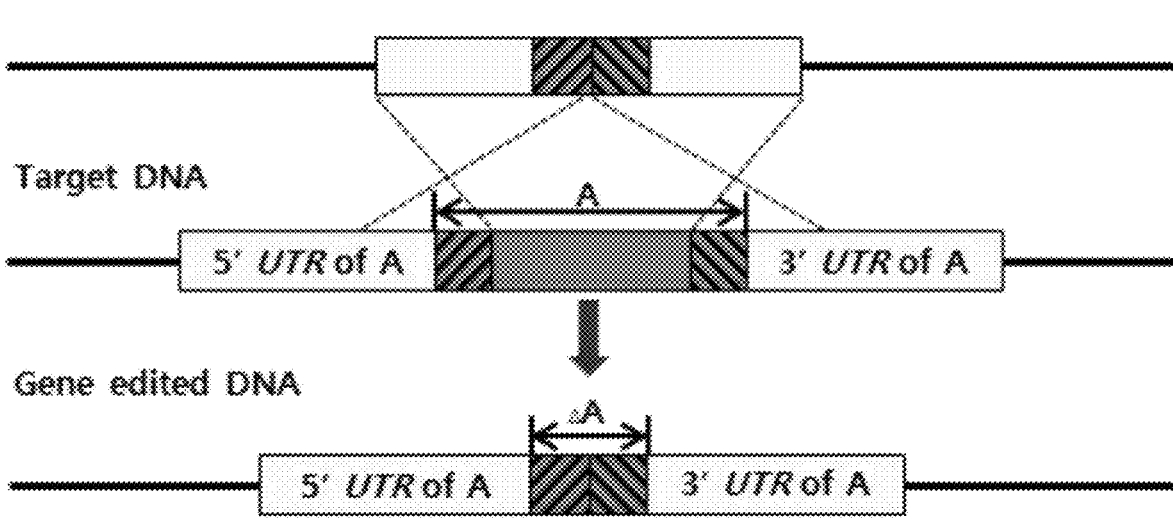

FIGS. 1A and 1B schematically show the genetically engineered site of the microorganism according to the example. FIG. 1A shows the process of replacing the protease gene (htrA or pepN) with the VIP gene to improve VIP productivity. A signal peptide that assists in secretion on 5'-side of the VIP gene and a tag for detection on 3'-side of the VIP gene were included in one cassette. The protease gene is *L. brevis* htrA (SEQ ID NO: 14) or *L. brevis* pepN (SEQ ID NO: 15). FIG. 1B shows a process of generating an auxotroph to promote environmental safety, by removing some regions of a target gene. The target gene is *L. brevis* ribB (SEQ ID NO: 18). Each abbreviation in FIGS. 1A and 1B has the following meaning: P: Promoter, SP: Signal peptide, UTR: Untranslated region, VIP: Vasoactive intestinal peptide), A: *L. brevis* ribB, B: *L. brevis* htrA or *L. brevis* pepN.

Example 2: Confirmation of Generation of Recombinant Microorganism

PCR was proceeded to confirm that the recombinant microorganism was produced as intended. Lactic acid bacteria colonies stationary cultured at 37° C. for 16 hours on a De Man, Rogosa and Sharpe agar (MRS) plate were used. A single colony was picked and suspended in a tube containing 100 μl of distilled water. After bead-beating, the suspension was heated at 98° C. for 10 minutes to use as a DNA template. 1 μl of DNA template, 1 μl of forward primer, 1 μl of reverse primer, and 25 μl of DNA polymerase mix were mixed to prepare a PCR mixture. PCR was performed under the conditions of 40 cycles of amplification of (a) denaturation, 10 seconds at 98° C.; (b) annealing, 15 seconds at 55° C.; and (c) extension, 10 seconds at 72° C. per cycle, and a final extension of 2 minutes at 72° C. The primers used were designed to target regions outside the open reading frame (ORF) of the gene region to be engineered, and the sequences are described in Table 1 below.

TABLE 1

| Name | Sequence | SEQ ID NO |
|------|----------|-----------|
| 1-46 pepN icF | AGC AAC CTT TGA CCT AGC | 21 |
| 1-46 pepN icR | AAT TCC ATA TCA CCA CCC AC | 22 |
| pepN orf cF | CCC GAT GGC CTT ACA AC | 23 |
| pepN orf cR | GGA ACG GCT GTC CAT TAG | 24 |

TABLE 1-continued

| Name | Sequence | SEQ ID NO |
|------|----------|-----------|
| 1-46 htrA insert cF | CTA AAT GAG GAG GGT TCG CG | 25 |
| 1-46 htrA insert cR | AAG CTG GCG CTT TCA TTC C | 26 |
| 1-46 htrA ORF cF | ACC TCT AAC GTC AAC GTC | 27 |
| 1-46 htrA ORF cR | AGT TCC CAG GGT TAA TCG | 28 |

Figure 2A:
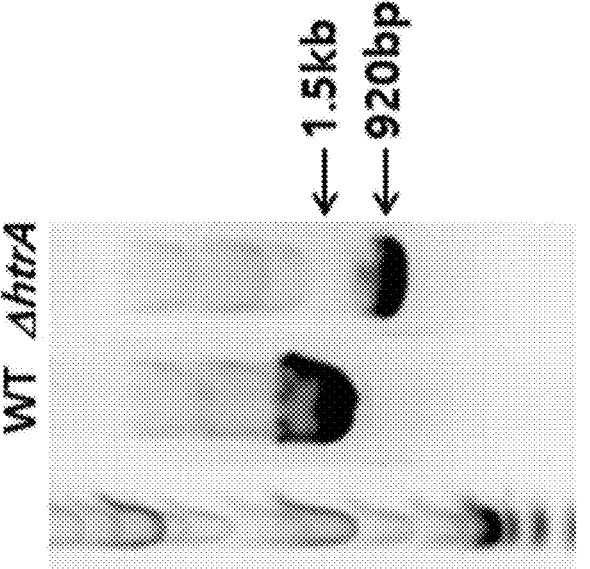
FIGS. 2A and 2B are figures confirming the generation of recombinant microorganisms with improved VIP productivity, according to an example.
Figure 2A:
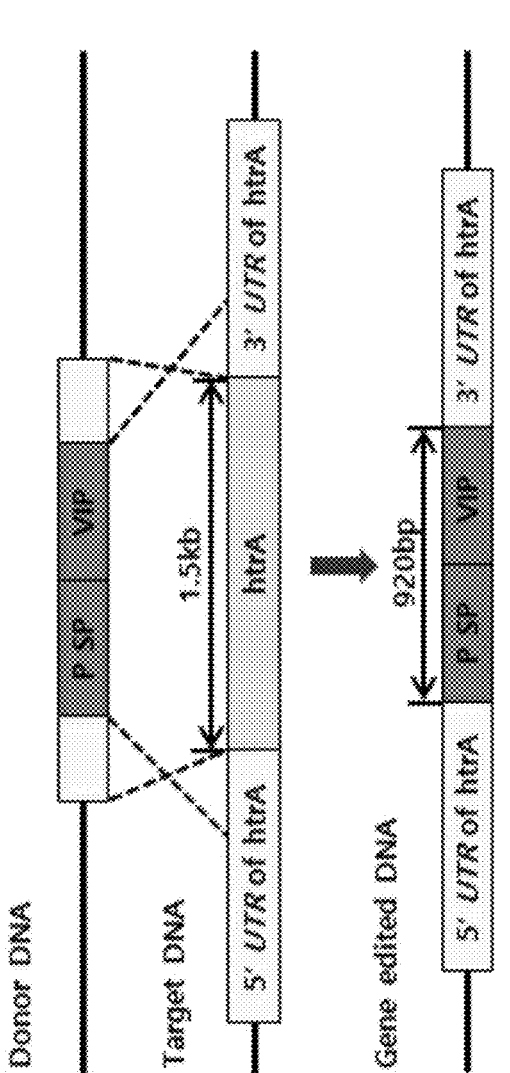
Figure 2B:
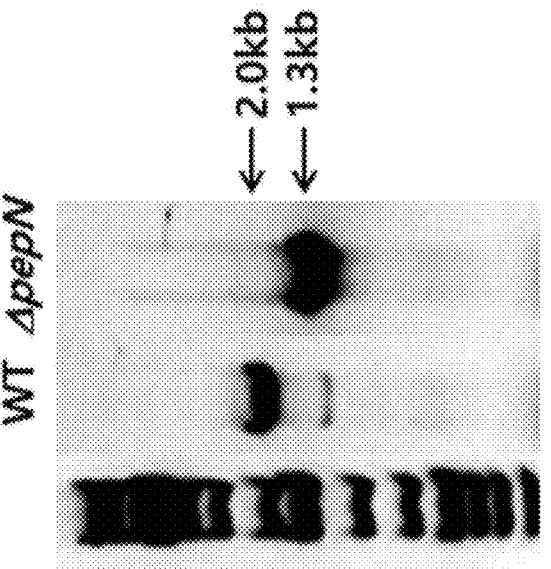
Figure 2B:
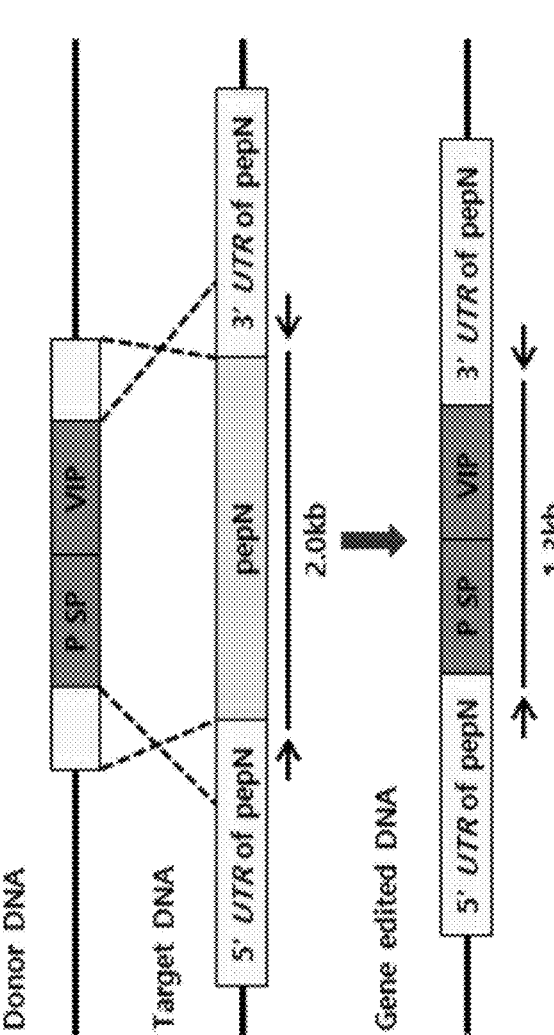

The results are each shown in FIGS. 2A and 2B. More specifically, FIGS. 2A and 2B are schematics (left) showing that the protease genes htrA (FIG. 2A) and pepN (FIG. 2B) are each replaced with a VIP expression cassette, and gel images (right) showing that the band sizes were changed as intended due to generation of recombinant microorganisms. As shown in FIGS. 2A and 2B, it was confirmed that recombinant microorganisms were generated in which the protease genes htrA and pepN were each replaced with a VIP expression cassette. In case of htrA, the band size of the PCR product was 1.5 kb in the wild-type, and when the htrA region was replaced with a VIP expression cassette, the band size was 920 bp. In case of pepN, the band size of the PCR product was 2 kb in the wild-type, and when the pepN region was replaced with a VIP expression cassette, the band size was 1.3 kb. In the schematics of FIGS. 2A and 2B, each abbreviation is as defined in Example 1, and WT in the gel image refers to the wild-type.

Example 3: Evaluation of VIP Productivity of Recombinant Microorganism

In order to identify whether the VIP productivity of the recombinant microorganism was improved, an evaluation was performed to identify the VIP expression level of the strains prepared in Example 1. The stock of the prepared strain was streaked on an MRS plate and stationary cultured for 3 days at 37° C. Here, a single colony was picked and cultured with shaking at 37° C. in a MRS liquid medium for 24 hours. The cultured medium was inoculated into 25 ml of MRS so that $OD_{600}$ became 0.1, and then cultured with shaking at 37° C. for 16 hours. 10 ml of the strain culture medium was extracted and centrifuged at 4,000 rpm for 10 minutes, and only the supernatant was extracted, 1 ml of tricholoacetic acid (TCA) was added, and treated at 4° C. for 30 minutes or more. This was centrifuged at 10,000 rpm for 10 minutes, the supernatant was removed and the pellet was suspended using 1 ml of acetone stored at 4° C. After centrifugation at 13,000 rpm for 10 minutes, the supernatant was removed, and 0.5 ml of acetone was added to suspend the pellet. The suspension was again centrifuged at 13,000 rpm for 10 minutes, and dried at 60° C. for 5 minutes. A sample buffer (reducing buffer) was added and the pellet was mixed well and treated at 98° C. for 10 minutes. Western blotting was performed using the obtained solution. Based on the results of the western blotting, the intensities of the bands measured according to regions of the same size were quantified by using a program called ImageJ.

Figure 3A:
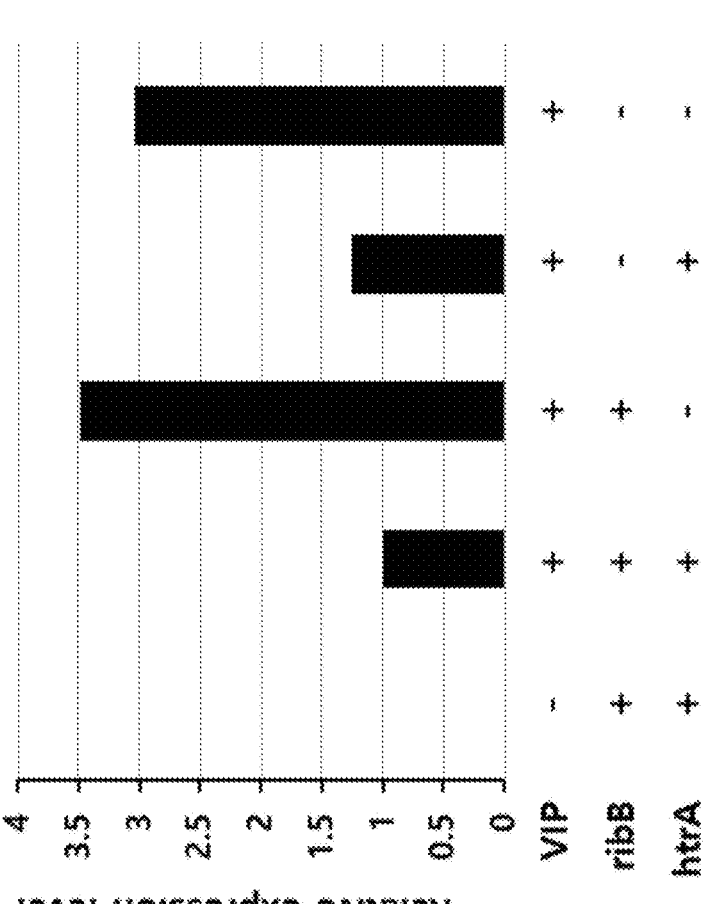
FIGS. 3A and 3B are figures showing that recombinant microorganisms according to an example had improved VIP productivity.
Figure 3A:
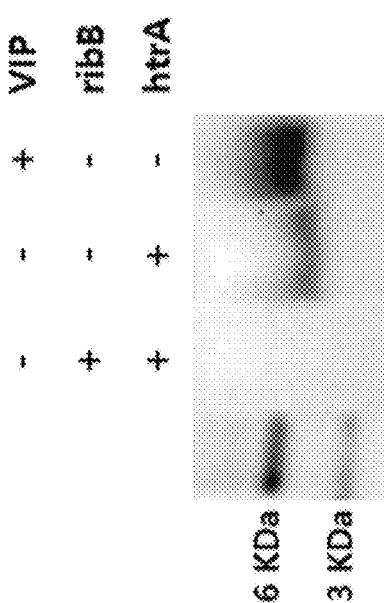
Figure 3B:
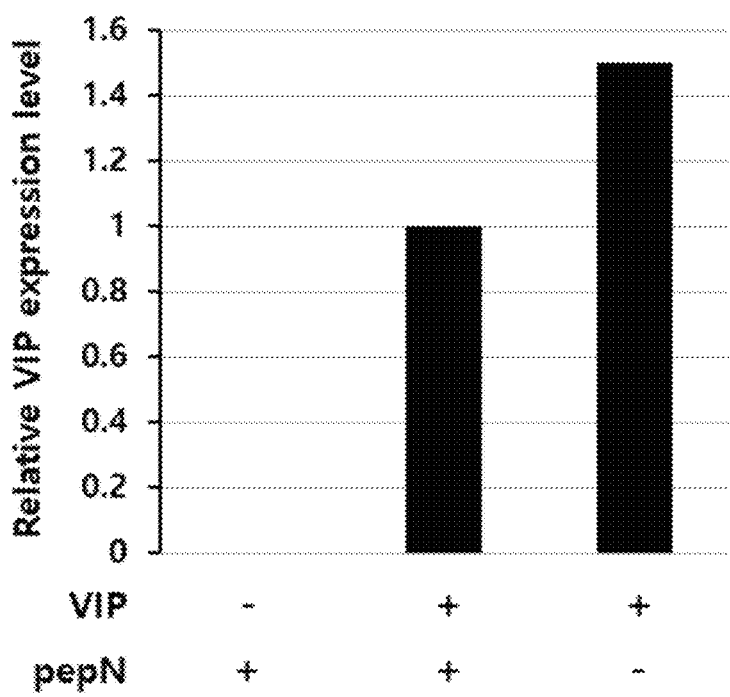

The results are each shown in FIGS. 3A and 3B. More specifically, FIG. 3A is a gel image (left) showing the generated recombinant strain in which htrA and/or ribB is deleted, and VIP expressed therefrom, and a graph (right) quantifying expression level of VIP. FIG. 3B is a graph showing expression level of VIP expressed from a recombinant strain in which pepN is deleted. As may be identified from FIGS. 3A and 3B, when the protease gene was deleted from *L. brevis*, the expression level of VIP, an effective substance, was increased. In particular, when htrA was deleted, the expression level of the target substance, VIP, was increased more than 3 times compared to those when other genes were deleted.

Example 4: Confirmation of Generation of Auxotrophs

PCR was performed to confirm that the auxotroph was generated as intended. Lactic acid bacteria colonies, which were stationary cultured at 37° C. for 16 hours on a De Man, Rogosa and Sharpe agar (MRS) plate, were used. A single colony was picked and suspended in a tube containing 100 µl of distilled water. After bead-beating, the suspension was heated at 98° C. for 10 minutes to use as a DNA template. 1 µl of DNA template, 1 µl of forward primer, 1 µl of reverse primer, and 25 µl of DNA polymerase mix were mixed to prepare a PCR mixture. PCR was performed under the conditions of 40 cycles of amplification of (a) denaturation, 10 seconds at 98° C.; (b) annealing, 15 seconds at 55° C.; and (c) extension, 10 seconds at 72° C. per a cycle, and a final extension of 2 minutes at 72° C. The primers used were designed to target regions inside and outside the ORF of the gene region to be engineered, and the sequences are described in Table 2 below.

TABLE 2

| Name | Sequence | SEQ ID NO |
|------|----------|-----------|
| 1-46 ribB orf cF | TAA CCG CAG TGA CTG AC | 29 |
| 1-46 ribB orf cR | AGC TGA TAC ATC AAA GGT C | 30 |
| 1-46 ribB icF | AGC ATT GTG TTA TCA GC | 31 |
| 1-46 ribB icR | GCA GCA TTG GTA GCA AC | 32 |
| LbthyA-UP-cF3 | GTG TGG CAA GGT GGC AAA GCC A | 33 |
| LbthyA-DN-cR1 | CCG ATC TAC AGG CCC AAC TCG ATG A | 34 |

Figure 4A:
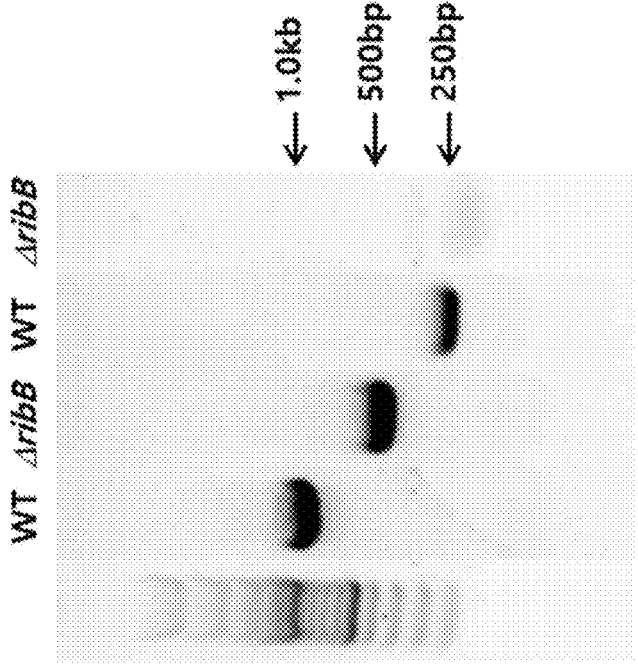
FIGS. 4A and 4B are figures confirming the generation of recombinant microorganisms with improved environmental safety, according to an example.
Figure 4A:
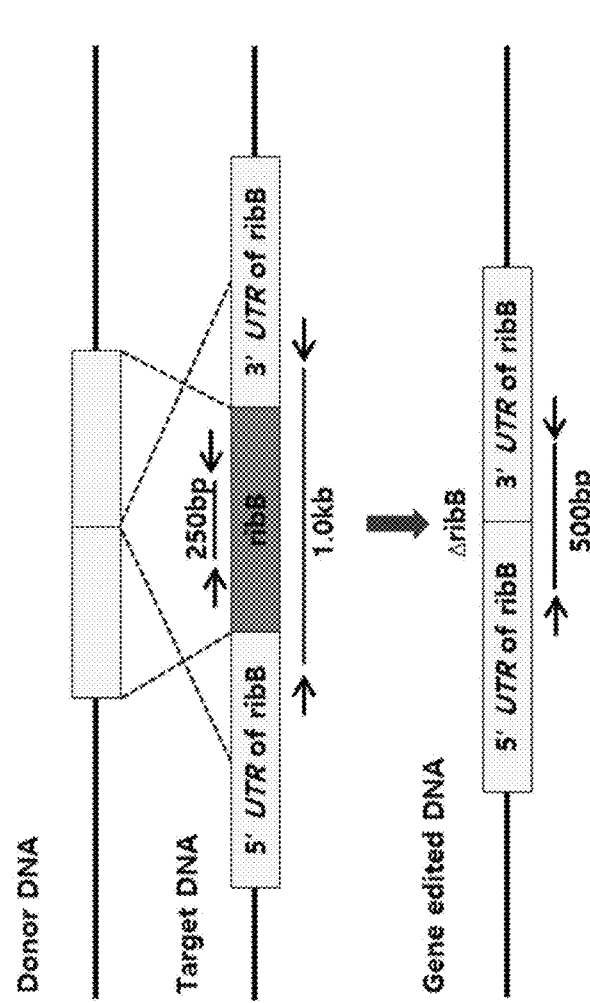
Figure 4B:
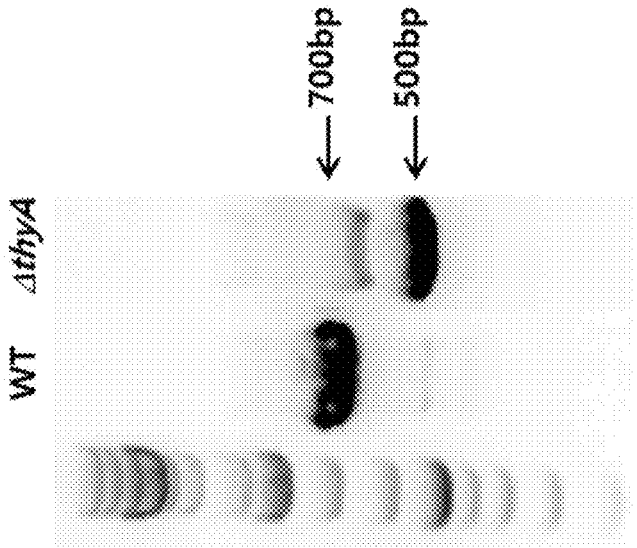
Figure 4B:
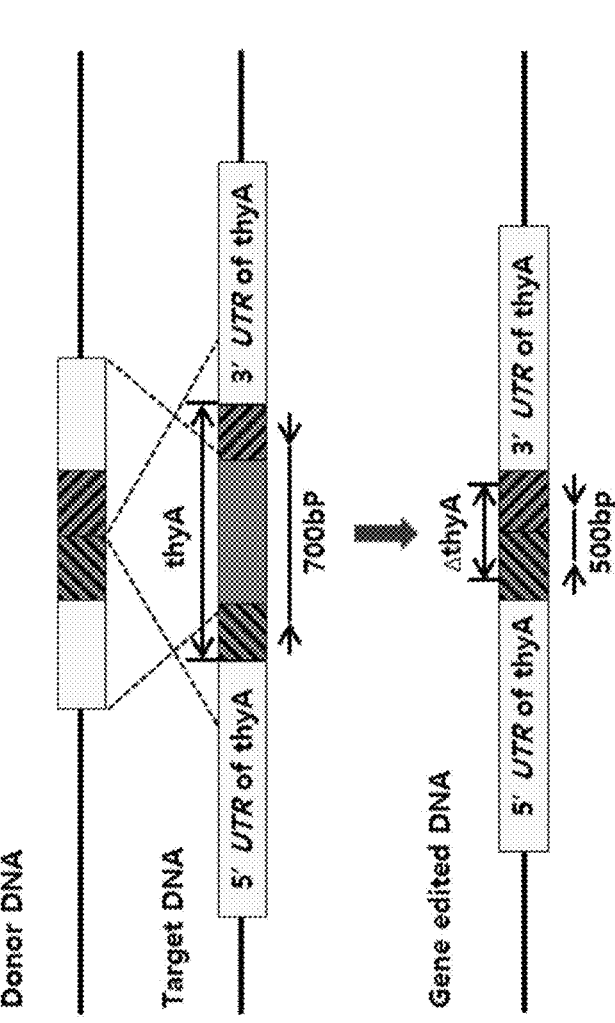

The results are each shown in FIGS. 4A and 4B. More specifically, FIGS. 4A and 4B are schematics (left) of recombinant microorganisms in which rib and thyA are deleted, respectively, and gel images (right) showing that the band sizes were changed as intended due to the generation of the recombinant microorganisms. In FIGS. 4A and 4B, each abbreviation is as defined in Example 1, and WT in the gel image refers to the wild-type. As shown in FIGS. 4A and 4B, it was confirmed that recombinant microorganisms were generated in which ribB and thyA were deleted, respectively.

In case of ribB, the band size of the PCR product was 1.0 kb in the wild-type, and when the ribB region was deleted, the band size was 500 bp. When PCR was performed using a primer that binds to the inside of the ribB region, the wild-type was found to be 250 bp, and no band was observed in the strain in which ribB was deleted. In case of thyA, the band size of the PCR product was 700 bp in the wild-type, and when a part of the thyA region was deleted, the band size was 500 bp.

Example 5: Evaluation of Environmental Safety of Auxotroph

A growth test was performed to determine the growth pattern of the strain prepared in Example 1. The stock of the prepared strain was streaked on an MRS plate and stationary cultured for 3 days at 37° C. From the plate, a single colony was picked and cultured with shaking (230 rpm) in an MRS liquid medium at 37° C. for 24 hours. 1 ml of the culture medium was extracted and centrifuged at 13,000 rpm for 1 minute. After suspending the cell pellet in 1 ml of 1×PBS solution, the cell was inoculated into 25 ml of a minimum medium for lactic acid bacteria which could limit the growth of lactic acid bacteria called semi-defined media (SDM), so that the measured $OD_{600}$ became 0.0025. It was cultured for 40 hours under a shaking culture (230 rpm) condition at 37° C., and the measured $OD_{600}$ values at 15, 17, 20, 22, 24, and 40 hours after inoculation are shown as a graph.

Figure 5A:
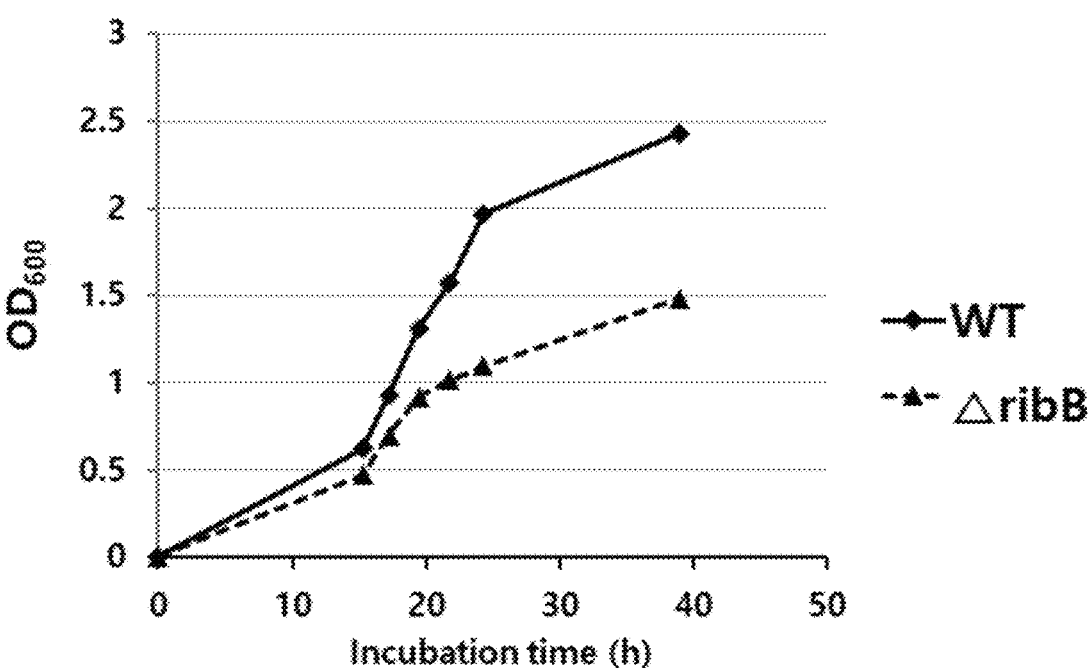
FIGS. 5A and 5B are graphs showing recombinant microorganisms according to an example had improved environmental safety.
Figure 5B:
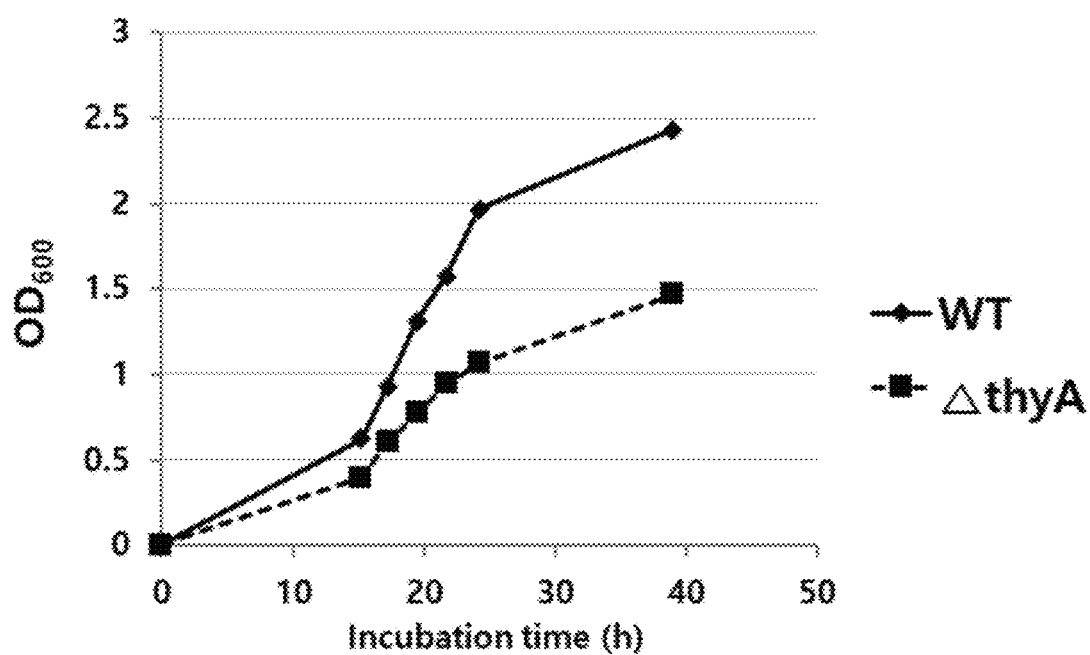

The results are each shown in FIGS. 5A and 5B. More specifically, FIGS. 5A and 5B are graphs showing the growth patterns of ribB-deleted recombinant lactic acid bacteria (FIG. 5A) and thyA-deleted recombinant lactic acid bacteria (FIG. 5B). In FIGS. 5A and 5B, WT means wild-type. It was confirmed from FIGS. 5A and 5B that the growth of the auxotrophic lactic acid bacteria has been inhibited in nutrient-deficient medium conditions.

Example 6: In Vivo Efficacy: IBD Animal Model Experiment

In order to evaluate therapeutic efficacy of VIP protein derived from the transformed strain, the transformed strain was orally administered to mouse intestinal inflammation models induced by dextran sulfate sodium (DSS), and then the survival rate or disease activity index (DAI) score were identified. After primarily culturing in 5 ml of MRS medium for one day, the cultured strain was inoculated into 50 ml of MRS medium so that $OD_{600}$ became 0.1. When the $OD_{600}$ of the culture medium reached 4 to 5 after 16 to 18 hours, the strain was recovered according to the total number of mice to be administered and the number of feedings. The culture supernatant was removed by centrifugation at 4,000 rpm for 10 minutes, and the recovered strain was suspended in 1×PBS so that it could be administered at $1\times10^9$ cfu per mouse per administration. The administration of the strain was performed once a day, for a total of 16 days.

The treatment efficacy experiment was started by setting the first day of administrating the strain to Day-9, and from Day 0 to Day 5, 2% DSS was in drinking water in all groups except for the PBS group, and euthanasia was performed on Day 8. After DSS treatment, the DAI score was calculated by checking the weight loss, bristled hair, the degree of movement of the animals and the presence of diarrhea every two days.

Figure 6:
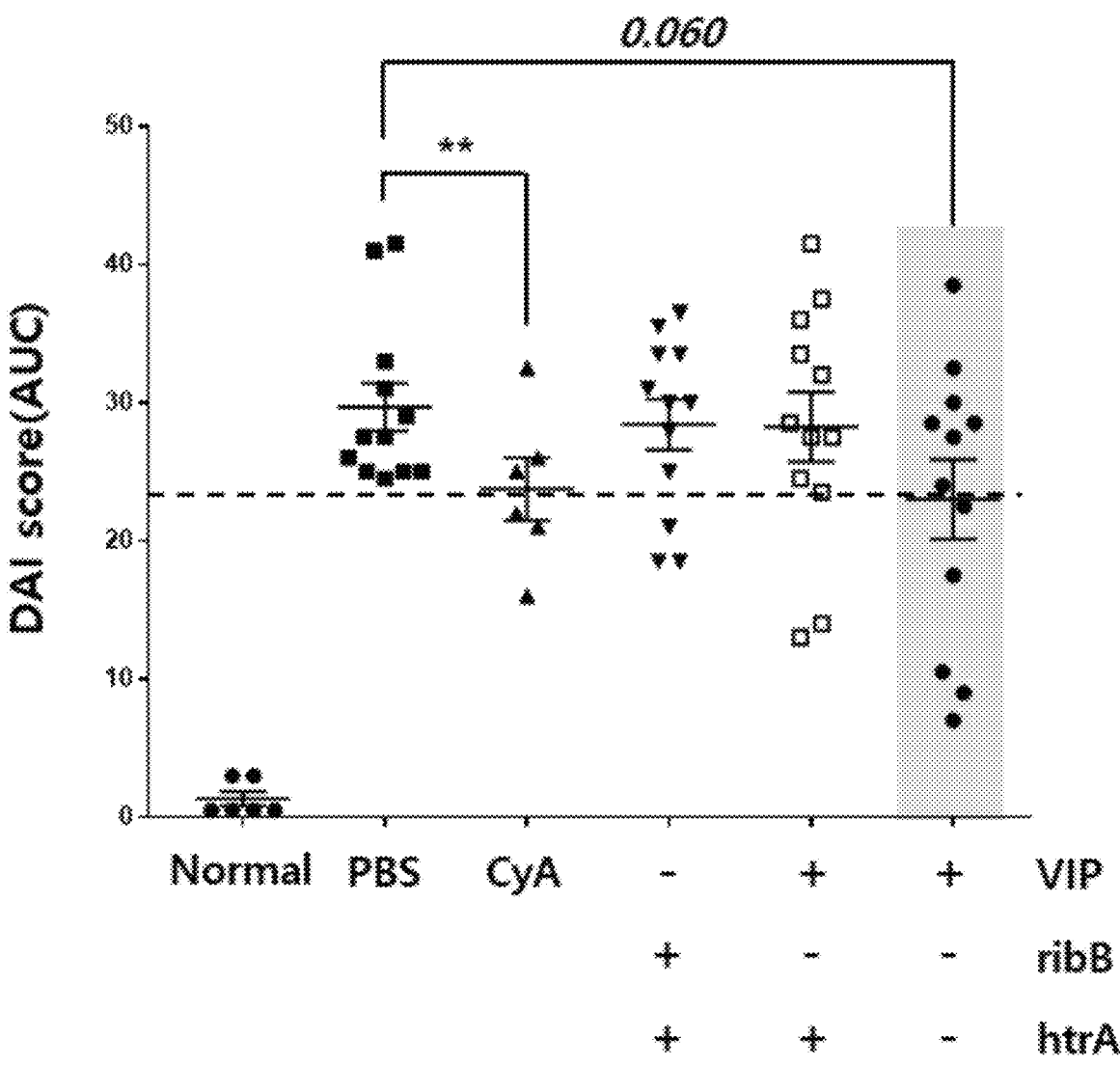
FIG. 6 is a graph showing that a recombinant microorganism according to an example exhibits a therapeutic effect on IBD in an animal model.

The results are shown in FIG. 6. As shown in FIG. 6, it was confirmed that the strain having improved productivity and improved environmental safety exhibited superior efficacy compared to the control groups in the IBD animal model experiment.

ACCESSION NUMBER

Depository institute: Korea Research Institute of Bioscience and Biotechnology
Accession number: KCTC13421BP
Deposition date: 2017 Dec. 12
Depository institute: Korea Research Institute of Bioscience and Biotechnology
Accession number: KCTC13422BP
Deposition date: 2017 Dec. 12
Depository institute: Korea Research Institute of Bioscience and Biotechnology
Accession number: KCTC13423BP
Deposition date: 2017 Dec. 12

The invention claimed is:

1. A recombinant microorganism of the genus *Lactobacillus*, in which a constitutive promoter and an exogenous gene are introduced and a protease is inactivated, wherein the exogenous gene is operably linked to the constitutive promoter and encodes a vasoactive intestinal peptide (VIP), wherein the inactivated protease is at least one selected from the group consisting of HtrA, PepN, ClpP, and Lon, and wherein the microorganism is *Lactobacillus paracasei, Lactobacillus brevis*, or *Lactobacillus plantarum*.

2. The microorganism of claim 1, further comprising a signal sequence operably linked between the constitutive promoter and the exogenous gene.

3. The microorganism of claim 1, wherein gene encoding the protease is replaced with an exogenous gene operably linked to the constitutive promoter and encoding the VIP.

4. The microorganism of claim 1, wherein the microorganism is an auxotroph.

5. The microorganism of claim 4, wherein at least one gene selected from the group consisting of ribB, thyA, and glmS is deleted.

6. A composition for treating a disease causing damage to gastrointestinal tract in humans, comprising the recombinant microorganism as set forth in claim 1.

7. The composition of claim 6, wherein the disease is one causing inflammation of the gastrointestinal tract.

8. The composition of claim 7, wherein the disease is at least one selected from the group consisting of inflammatory bowel disease (IBD) and colitis.

9. The composition of claim 8, wherein the inflammatory bowel disease is ulcerative colitis or Crohn's disease.

\* \* \* \* \*